US012485255B2

(12) United States Patent
Gilmartin et al.

(10) Patent No.: US 12,485,255 B2
(45) Date of Patent: Dec. 2, 2025

(54) DELIVERY SYSTEMS FOR DEVICES WITH UNSUPPORTED STRUCTURE

(71) Applicant: Boston Scientific Scimed, Inc., Maple Grove, MN (US)

(72) Inventors: Gary Gilmartin, Foxford (IE); Geraldine A. Toner, Raphoe (IE); Martyn G. Folan, Galway (IE); Daniel Tuck, Galway (IE); Thomas M. Keating, Galway (IE)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 789 days.

(21) Appl. No.: 16/845,854

(22) Filed: Apr. 10, 2020

(65) Prior Publication Data

US 2020/0324093 A1 Oct. 15, 2020

Related U.S. Application Data

(60) Provisional application No. 62/832,762, filed on Apr. 11, 2019.

(51) Int. Cl.
*A61M 25/10* (2013.01)
*A61M 25/00* (2006.01)

(52) U.S. Cl.
CPC .... *A61M 25/1011* (2013.01); *A61M 25/1018* (2013.01); *A61M 25/1025* (2013.01); *A61M 2025/0018* (2013.01)

(58) Field of Classification Search
CPC .......... A61M 25/1011; A61M 25/1018; A61M 25/10; A61M 25/1009; A61M 25/04;
(Continued)

(56) References Cited

U.S. PATENT DOCUMENTS 5,389,106 A * 2/1995 Tower ........................ A61F 2/88 606/198
5,709,701 A * 1/1998 Parodi ........................ A61F 2/07 623/1.11
(Continued)

FOREIGN PATENT DOCUMENTS

WO 2015095416 A1 6/2015
WO 2017062753 A1 4/2017

OTHER PUBLICATIONS

International Search Report and Written Opinion for the International Patent Application No. PCT/US2020/027712, mailed Aug. 10, 2020, 12 pages.

*Primary Examiner* — Kevin C Sirmons
*Assistant Examiner* — Alexandra Lalonde
(74) *Attorney, Agent, or Firm* — Seager, Tufte & Wickhem, LLP

(57) ABSTRACT

The present disclosure relates generally to the field of medical devices and medical device delivery. In particular, the present disclosure relates to medical devices and delivery systems for positioning and delivering medical devices with an unsupported structure, for example, within a distant and/or tortuous portion of body lumen. For example, a delivery system may position a supported structure of a medical device within a proximal portion of a body lumen and an unsupported structure of the medical device within a distal portion of the body lumen. Examples include delivery systems within an unsupported structure of a medical device to be delivered, wherein a number of balloons are arranged un-inflated within an unsupported structure, with a distal balloon removably attached to a distal portion of the unsupported structure, and the balloons are inflatable in series to deploy the unsupported structure linearly from a distal end of the delivery system.

8 Claims, 12 Drawing Sheets

(58) Field of Classification Search

CPC .. A61M 2025/0018; A61M 2025/1013; A61M 2025/1059; A61M 2025/1081; A61M 2025/1068; A61M 25/1025; A61M 25/10184; A61M 25/10185; A61M 25/10186; A61M 25/1027; A61M 25/0074; A61M 2025/1004; A61M 2025/1015; A61M 2025/1043; A61M 2025/1045; A61M 2025/1052; A61M 2025/1061; A61M 2025/1072; A61M 2025/1093; A61M 2210/1042; A61M 2210/1053; A61M 2210/1057; A61M 2210/106; A61F 2/958; A61F 2/962; A61F 2002/9583; A61F 5/0003; A61F 5/003; A61F 2250/0007

See application file for complete search history.

(56) References Cited

U.S. PATENT DOCUMENTS 5,820,595 A * 10/1998 Parodi .................... A61F 2/958 604/101.05
6,325,820 B1 * 12/2001 Khosravi .................. A61F 2/92 623/1.13
6,896,694 B1 * 5/2005 Filho ...................... A61F 2/958 623/1.11
2002/0198559 A1 * 12/2002 Mistry .................. A61M 25/10 604/103.1
2005/0192614 A1 9/2005 Binmoeller
2006/0155367 A1 * 7/2006 Hines .................... A61F 2/9526 623/1.28
2006/0229700 A1 * 10/2006 Acosta .................... A61F 2/958 623/1.11
2007/0067012 A1 * 3/2007 George ................... A61F 2/915 623/1.12
2007/0173924 A1 * 7/2007 Gelbart ..................... A61F 2/88 623/1.15
2008/0133000 A1 * 6/2008 Molony .................... A61F 2/91 623/1.35
2009/0125094 A1 * 5/2009 Rust .......................... A61F 2/95 623/1.12
2009/0187240 A1 * 7/2009 Clerc ...................... A61F 2/848 623/1.22
2013/0289690 A1 * 10/2013 Thapliyal .................. A61F 2/90 53/425
2016/0045341 A1 * 2/2016 Aggerholm ........... A61M 31/00 623/1.11
2016/0051799 A1 * 2/2016 Daniels ................. A61M 25/10 604/103.11
2020/0281711 A1 * 9/2020 McDermott .............. A61F 2/07

* cited by examiner

DELIVERY SYSTEMS FOR DEVICES WITH UNSUPPORTED STRUCTURE

CROSS REFERENCE TO RELATED APPLICATIONS

The present application claims the benefit of priority under 35 U.S.C. § 119 to U.S. Provisional Patent Application Ser. No. 62/832,762, filed on Apr. 11, 2019, which is incorporated by reference in its entirety for all purposes.

FIELD

The present disclosure relates generally to the field of medical devices and medical device delivery. In particular, the present disclosure relates to a medical device, method and delivery system for positioning a medical device with an unsupported structure within a distant and/or tortuous portion of body lumen.

BACKGROUND

Conventional endoscopic delivery systems used to deliver medical devices (e.g., stents, clips, etc.) into body lumens and/or passages tend to be rigid to allow for tracking through tortuous anatomies or require a previously positioned ancillary device (e.g., guidewire, endoscope, etc.) to reach a target location. Certain body lumens may be too inaccessible and/or tortuous to safely and efficiently access the target location using these conventional systems or techniques. This problem tends to be amplified when a substantial portion of the medical device includes an unsupported structure that may lack the requisite rigidity to be delivered without the benefit of a previously positioned ancillary device.

A variety of advantageous medical outcomes may therefore be realized by the medical devices and medical device delivery systems of the present disclosure.

SUMMARY

In one aspect, the present disclosure relates to a medical device delivery system comprising an elongate member and a medical device disposed within a distal portion of the elongate member. The medical device may include a proximal supported structure and a distal unsupported structure. The medical device may be configured to move from a first position, in which the supported structure is disposed within the distal portion of the elongate member in a first configuration, and a second position in which the supported structure extends beyond a distal end of the elongate member in a second configuration. A plurality of balloons may be disposed within the distal portion of the elongate member and the unsupported structure. A fluid delivery lumen may extend through the elongate member. A proximal end of the fluid delivery lumen may be configured to fluidly connect to a fluid source and a distal end of the fluid delivery lumen may be in fluid communication with the plurality of balloons. Each balloon of the plurality of balloons may be in a concertinaed configuration. The unsupported structure may be in a concertinaed configuration over the plurality of balloons. A distal end of the unsupported structure may be attached to a distal balloon of the plurality of balloons.

In the described and other embodiments, the plurality of balloons may include a proximal balloon, a distal balloon and one or more intermediate balloons extending between the proximal and distal balloons. A proximal end of the proximal balloon may include an opening configured to fluidly receive the distal end of the fluid delivery lumen. A distal end of the distal balloon may be sealed. Adjacent balloons of the plurality of balloons may be attached by a flexible connector. The flexible connector may include a lumen extending therethrough such that adjacent balloons are in fluid communication with each other. The flexible connectors between adjacent balloons may provide fluid communication therebetween along a length of the plurality of balloons. The flexible connector may be configured to provide a flexible junction between adjacent balloons as the plurality of balloons move from the concertinaed configuration to a linearly expanded configuration. A plug may be removably disposed within the lumen of the flexible connector. The plug may be configured to prevent or limit a flow of inflation fluid into one or more of the plurality of balloons until a proximally adjacent balloon is in a linearly expanded configuration. The plurality of balloons may be configured to linearly expand sequentially from a proximal to distal direction. The unsupported structure may move from the concertinaed configuration to a linearly extended configuration as the balloons move from the concertinaed configuration to the linearly expanded configuration. The unsupported structure may linearly extend and be pulled distally along with the sequentially linearly expanding plurality of balloons. The supported structure may be configured to anchor the medical device within a body lumen. The sequentially linearly expanded plurality of balloons may be configured to pull the linearly extended unsupported structure into a distal portion of the body lumen. An inner surface of the unsupported structure may be attached to an outer surface of one or more of the plurality of balloons. The supported structure in the second position may include a flared flange, a cylindrical portion distal to the flared flange and an elastomeric membrane extending between the flared flange and cylindrical portion. The flared flange and cylindrical portion may be configured to anchor the medical device across a pylorus of a patient. The unsupported structure may include an impermeable liner.

In another aspect, the present disclosure relates to a medical device comprising a proximal supported structure and a distal unsupported structure. The unsupported structure may include distal end deployable from an elongate delivery member. A plurality of balloons may be deployable from within the unsupported structure and removably attached to the distal end thereof. The balloons may be configured in a concertinaed configuration, when undeployed, and are inflatable in series distally from the elongate delivery member, when deployed. The unsupported structure may be configured in a concertinaed configuration, when undeployed, and may unfold distally as the balloons are inflated, when deployed.

In the described and other embodiments, the plurality of balloons may include a proximal balloon, a distal balloon and one or more intermediate balloons extending between the proximal and distal balloons. A proximal end of the proximal balloon may include an opening configured to fluidly receive the distal end of the fluid delivery lumen. A distal end of the distal balloon may be sealed. Adjacent balloons of the plurality of balloons may be attached by a flexible connector. The flexible connector may include a lumen extending therethrough such that adjacent balloons are in fluid communication with each other. The flexible connectors between adjacent balloons may provide fluid communication therebetween along a length of the plurality of balloons. The flexible connector may be configured to provide a flexible junction between adjacent balloons as the plurality of balloons move from the concertinaed configuration to a linearly expanded configuration. A plug may be removably disposed within the lumen of the flexible connector. The plug may be configured to prevent or limit a flow of inflation fluid into one or more of the plurality of balloons until a proximally adjacent balloon is in a linearly expanded configuration. The plurality of balloons may be configured to linearly expand sequentially from a proximal to distal direction. The unsupported structure may move from the concertinaed configuration to a linearly extended configuration as the balloons move from the concertinaed configuration to the linearly expanded configuration. The unsupported structure may linearly extend and be pulled distally along with the sequentially linearly expanding plurality of balloons. The supported structure may be configured to anchor the medical device within a body lumen. The sequentially linearly expanded plurality of balloons may be configured to pull the linearly extended unsupported structure into a distal portion of the body lumen. An inner surface of the unsupported structure may be attached to an outer surface of one or more of the plurality of balloons. The supported structure in the second position may include a flared flange, a cylindrical portion distal to the flared flange and an elastomeric membrane extending between the flared flange and cylindrical portion. The flared flange and cylindrical portion may be configured to anchor the medical device across a pylorus of a patient. The unsupported structure may include an impermeable liner.

In yet another aspect, the present disclosure relates to a method of delivering a medical device with a body lumen. The method may include advancing a medical device delivery system into the body lumen. The medical device delivery system may include an elongate member and a medical device. The medical device may be disposed within the elongate member and include a distal unsupported structure. The method may further include introducing an inflation fluid into a proximal balloon of a plurality of balloons such that the proximal balloon moves from a concertinaed configuration to a linearly expanded configuration and a portion of the unsupported structure attached to the plurality of balloons moves from a concertinaed configuration to a linearly extended configuration to distally advance the unsupported structure through the body lumen.

In the described and other embodiments, introducing the inflation fluid into the plurality of balloons may sequentially move the plurality of balloons from the concertinaed configuration to the linearly expanded configuration and the unsupported structure attached to the plurality of balloons may moves from the concertinaed configuration to the linearly extended configuration to sequentially distally advance the unsupported structure. Adjacent balloons of the plurality of balloons may be attached by a flexible connector. The method may further include detaching the linearly expanded configuration of the plurality of balloons from the linearly extended configuration of the unsupported structure.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. In the figures.

DETAILED DESCRIPTION

The present disclosure is not limited to the particular embodiments described herein. The terminology used herein is for the purpose of describing particular embodiments only, and is not intended to be limiting beyond the scope of the appended claims. Unless otherwise defined, all technical terms used herein have the same meaning as commonly understood by one of ordinary skill in the art to which the disclosure belongs.

Although embodiments of the present disclosure are described with specific reference to a medical device delivery system for delivering a medical device (e.g., an anti-obesity device) with a supported portion and an unsupported portion across the pylorus and the duodenum and into a portion of the jejunum of a patient, it should be appreciated that such medical device delivery systems may be used to deliver a variety of medical devices (e.g., guidewires, access sheaths, cannulas, stents, catheters, etc.) into a variety of different body lumens and or passageways, including, for example, anal access to the transverse colon, ascending colon or ileum, Roux-en Y procedures, jejuncolic bypass procedures, jejunoileal bypass procedures, gastrectomy procedures, biliopancreatic diversion with duodenal switch (BPD-DS) procedures, gastrojejunostomy procedures, segmental colonic resection procedures, and the like.

As used herein, the singular forms “a,” “an,” and “the” are intended to include the plural forms as well, unless the context clearly indicates otherwise. It will be further understood that the terms “comprises” and/or “comprising,” or “includes” and/or “including” when used herein, specify the presence of stated features, regions, steps elements and/or components, but do not preclude the presence or addition of one or more other features, regions, integers, steps, operations, elements, components and/or groups thereof.

As used herein, the term “distal” refers to the end farthest away from the medical professional when introducing a device into a patient, while the term “proximal” refers to the end closest to the medical professional when introducing a device into a patient.

Figure 1A:
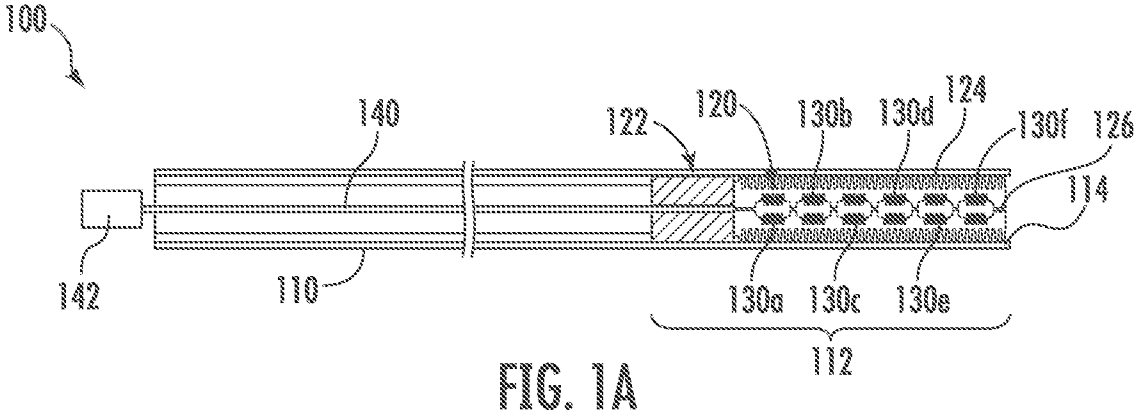
FIGS. 1A-1B provide perspective views of a medical device delivery system, according to one embodiment of the present disclosure.
Figure 1B:
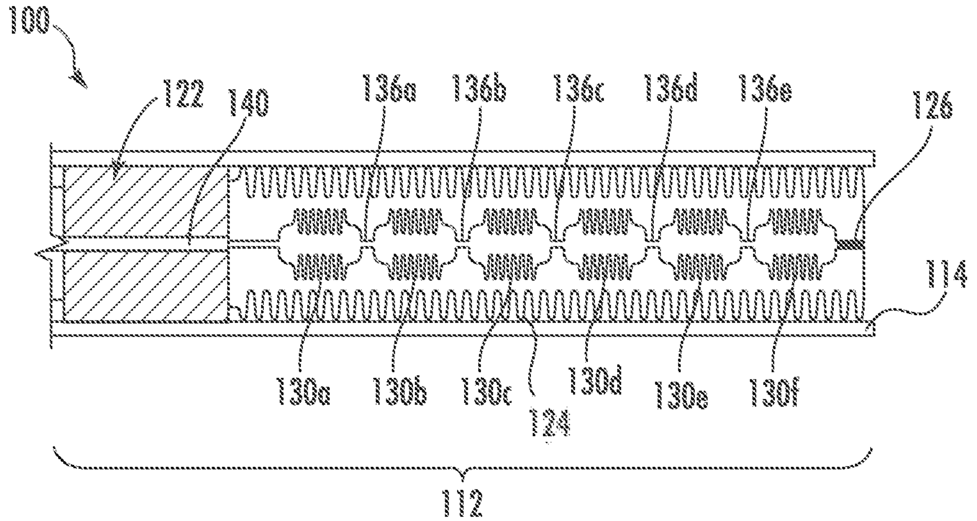

Referring to FIGS. 1A-1B, in one embodiment, a medical device delivery system 100 of the present disclosure may include an elongate member 110 (e.g., delivery catheter, endoscope, etc.) and a medical device 120 disposed (e.g., loaded) within a distal portion 112 of the elongate member 110. In various embodiments, the medical device 120 may include a first (e.g., proximal) supported structure 122 and a second (e.g., distal) unsupported structure 124. The elongate member 110 may be configured to move (e.g., slide, etc.) from a first position (e.g., distally extended) in which the supported structure 122 is disposed within the distal portion 112 of the elongate member 110 in a first configuration (e.g., constrained, non-expanded, non-deployed or delivery configuration, etc.) to a second position (e.g., proximally retracted) in which the supported structure 122 extends beyond a distal end 114 of the elongate member 110 in a second configuration (e.g., unconstrained, expanded, deployed, etc.).

A plurality of balloons 130 (e.g., non-compliant dilation balloons) may be disposed (e.g., loaded) in a tandem or linear configuration within (e.g., inside) the unsupported structure 124 of the medical device 120 and the distal portion 112 of the elongate member 110. In various embodiments, the plurality of balloons 130 may include a proximal balloon, a distal balloon and one or more intermediate balloons. For example, an embodiment of the present disclosure which includes six balloons in a tandem or linear configuration may include a proximal balloon 130*a* (e.g., first balloon progressing distally), a distal balloon 130*f* (e.g., sixth balloon progressing distally) and second 130*b*, third 130*c*, fourth 130*d* and fifth 130*e* intermediate balloons therebetween. Similarly, and by way of non-limiting example, an embodiment of the present disclosure which includes ten balloons may include a proximal balloon (e.g., first balloon) a distal balloon (e.g., tenth balloon) and second, third, fourth, fifth, sixth, seventh, eighth and ninth balloons therebetween. Each balloon 130*a*-130*f* of the plurality of balloons 130 may be disposed within the unsupported structure 124 and within the distal portion 112 of the elongate member 110 in a concertinaed configuration (e.g., collapsed in an accordion-like configuration). In addition, the unsupported structure 124 may be disposed in a concertinaed configuration over the respective outer surfaces of each of the plurality of concertinaed balloons 130*a*-130*f*. A distal end of the unsupported structure 124 may be attached to a distal end of the distal balloon 130*f* (e.g., the distal-most balloon of the plurality of balloons) by a release mechanism 126 (e.g., clip, hook, adhesive, perforated or frangible portion, etc.) as are commonly known in the art. In various additional embodiments, an inner surface of the unsupported structure 124 may be intermittently attached or glued to an outer surface of one or more of the balloons 130*a*-130*f*, e.g., using a silicone-based adhesive. Glue may be able to dissolve in the body to break the attachment. Other structure and/or function for detaching the unsupported structure from the balloons are contemplated as desired for a particular application. For example, different possibilities for detachment, include mechanical, chemical and/or electric based attachments, wherein the attachment between the unsupported structure and balloons may be broken by applying force to overcome a mechanical attachment, or an electrical current or chemical substance may act to sever the attachment.

A fluid delivery lumen 140 (e.g., inflation lumen) may extend through a full length of the elongate member 110, with a proximal end of the fluid delivery lumen configured to fluidly connect to a fluid source 142 (e.g., syringe, pump, etc.) and a distal end of the fluid delivery lumen in fluid communication with an opening in the proximal end of the proximal balloon 130*a* (e.g., the proximal-most balloon of the plurality of balloons) to deliver an inflation fluid (e.g. air, water, saline, etc.) from the fluid source 142 sequentially (e.g., from the proximal to distal direction) into each of the plurality of balloons 130*a*-130*f*.

In one embodiment, the proximal end of the proximal balloon 130*a* may include an opening in fluid communication with the distal end of a fluid delivery lumen 140 (as discussed above) and the distal balloon 130*f* may include a closed/sealed distal end. In various embodiments, adjacent balloons 130*a*-130*f* of the plurality of balloons 130 may be attached to each other by a flexible connector 136*a*, 136*b*, 136*c*, 136*d*, 136*e* (e.g., section of flexible tubing). Each of the flexible connectors 136*a*-136*e* may include an open lumen extending therethrough such that the adjacent balloons, and therefore each of the plurality of balloons including the proximal and distal balloons, are in fluid communication with each other. In addition to providing fluid communication between each of the plurality of balloons, the flexible connectors 136*a*-136*e* may also provide a flexible junction or pivot point between adjacent balloons to carry the unsupported structure 124 through challenging navigation paths, such as a tortuous anatomy, as the balloons 130*a*-130*f* sequentially move (e.g., in a proximal to distal direction) from a concertinaed configuration to a linearly expanded (e.g., elongated) configuration. For example, as each balloon 130*a*-130*f* sequentially moves from the concertinaed configuration to the linearly expanded configuration, the corresponding portion of the unsupported structure 124 may also move from the concertinaed configuration to a linearly extended configuration to "track" (e.g., pulled or carried distally) through the body lumen along with the sequentially linearly expanded configuration of the balloons. In embodiments of the present disclosure in which the concertinaed unsupported structure 124 and respective underlying concertinaed balloon(s) 130*a*-130*f* are attached (e.g., glued using a silicone-based adhesive), the linearly and/or outward expansion of the balloons may provide sufficient force (e.g., radial and/or longitudinal force) to break or otherwise disrupt the attachment point(s) to release the unsupported structure from the balloon(s).

Figure 2A:
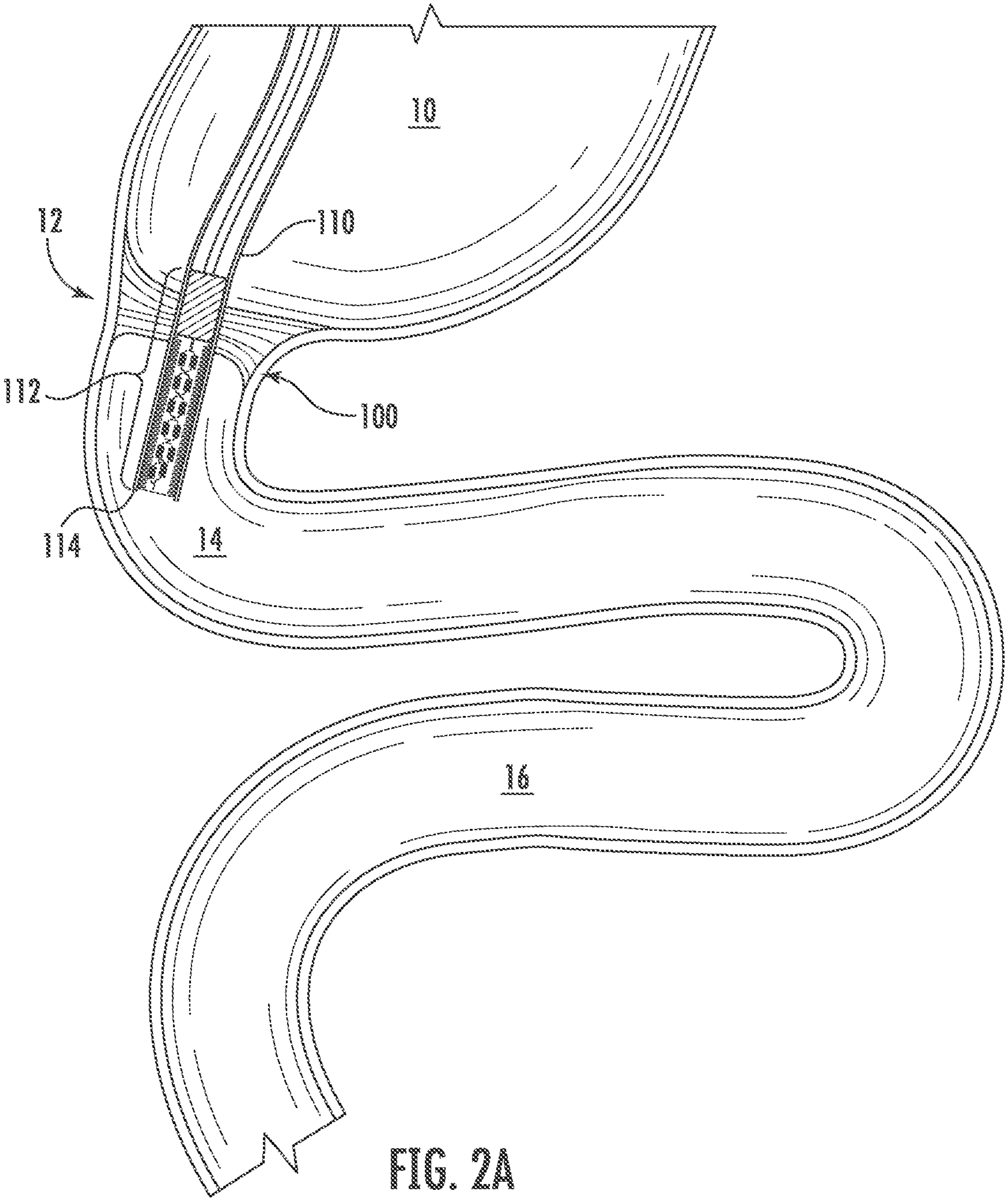
FIGS. 2A-2I illustrate representative steps of a medical device deployed within a body lumen using the medical device delivery system of FIGS. 1A-1B, according to one embodiment of the present disclosure.

Referring to FIGS. 2A-2I, in use and by way of example, the elongate member 110 of a medical device delivery system 100 of the present disclosure may be advanced through the esophagus and into a the stomach 10 of a patient, and the distal portion 112 of the elongate member 110 positioned across the pylorus 12 with the distal end 114 of the elongate member 110 extending into the duodenum 14 (FIG. 2A).

Figure 2B:
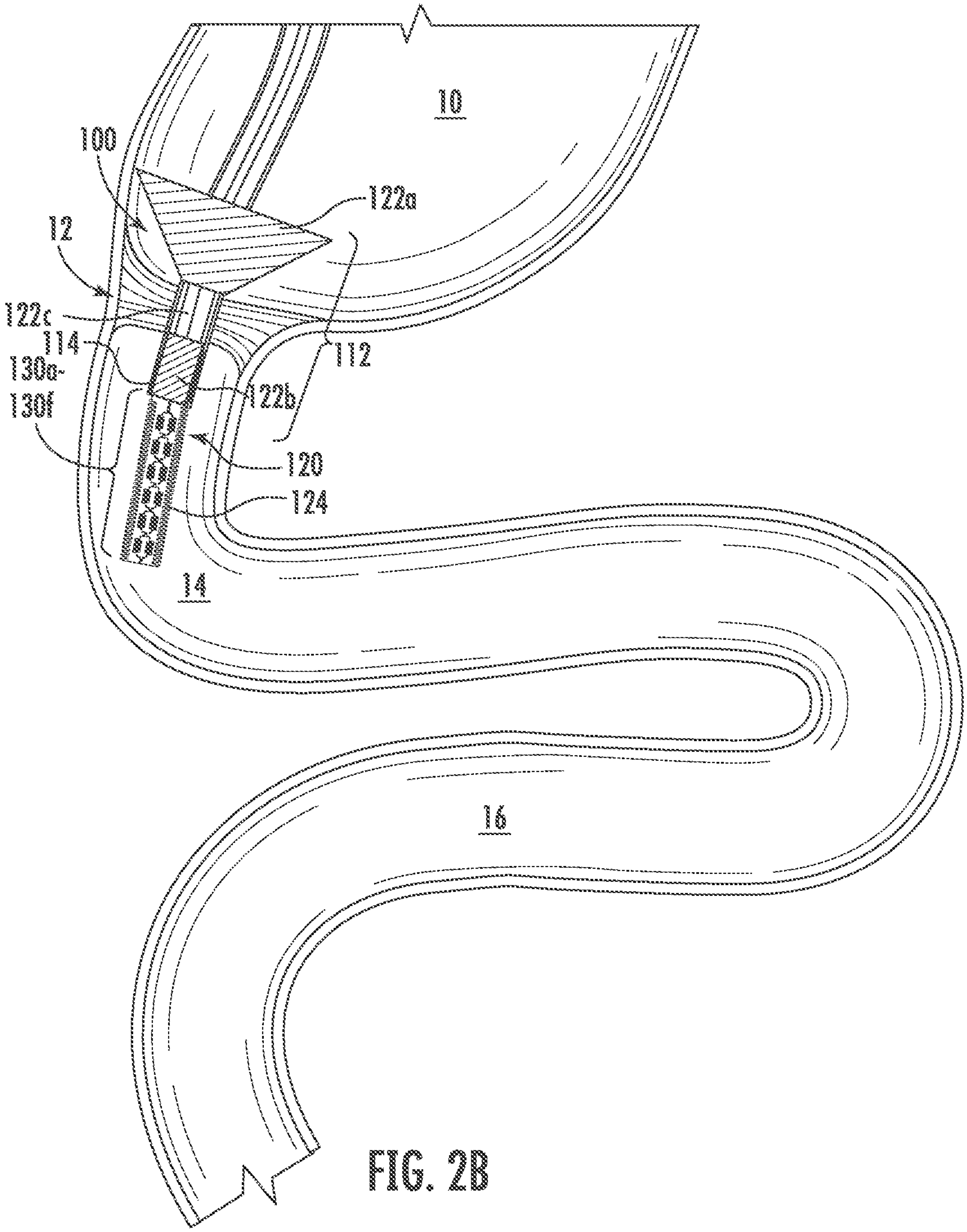

Referring to FIG. 2B, the distal portion 112 of the elongate member 110 may then be proximally retracted to advance (e.g., extend) the medical device 120 beyond the distal end 114 of the elongate member 110 (e.g., medical device 120 is deployed within the patient) with the supported structure positioned/anchored across the pylorus 12 in the second configuration and the unsupported structure 124 and balloons 130*a*-130*f* disposed within the duodenum 14 in the concertinaed configurations. In one embodiment, in the second configuration the supported structure 122 may include a self-expanding flared flange 122*a* (e.g., disposed within the stomach 10), a self-expanding cylindrical portion 122*b* distal to the flared flange 122*a* (e.g., disposed within the duodenum 14) and an elastomeric membrane 122*c* extending between, and connecting, the flared flange 122*a* and the cylindrical portion 122*b* (e.g., disposed across the pylorus 12). In various embodiments, the elastomeric membrane 122*c* may extend around an entire inner and/or outer surface of the flared flange 122*a* and/or cylindrical portion 122*b*. The unsupported structure 124 may include a sleeve or liner formed from or otherwise including an impermeable membrane (e.g., elastomeric membrane, etc.) attached to or integrally formed with an inner and/or outer surface of the cylindrical portion 122*b*. In various embodiments, the elastomeric membrane 122*c* and the unsupported structure 124 may include the same or different materials. In various additional embodiments, the elastomeric membrane 122*c* and the unsupported structure 124 may be formed from or otherwise include a single continuous (e.g., unitary) sheet of the elastomeric membrane.

Figure 2C:
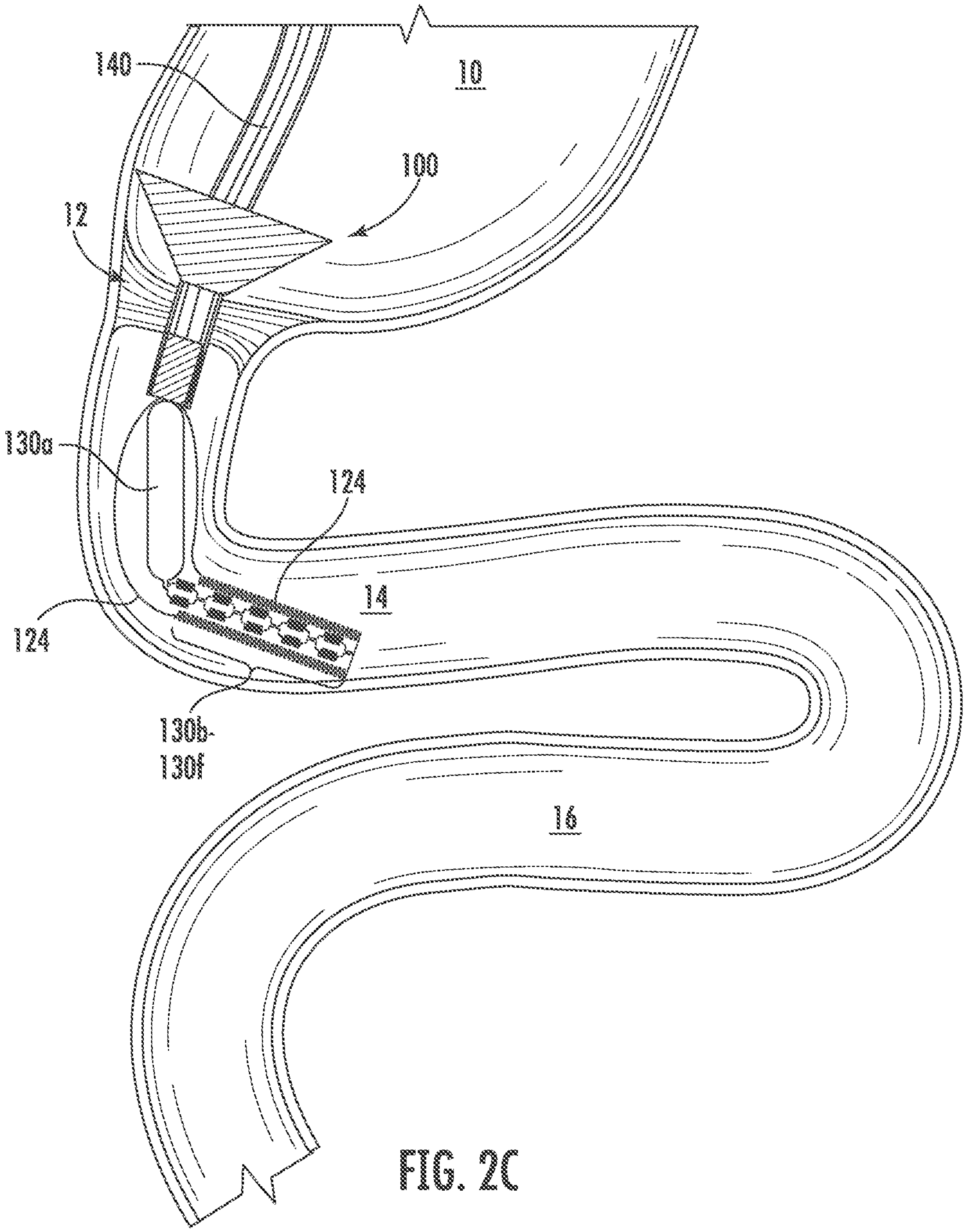
Figure 2D:
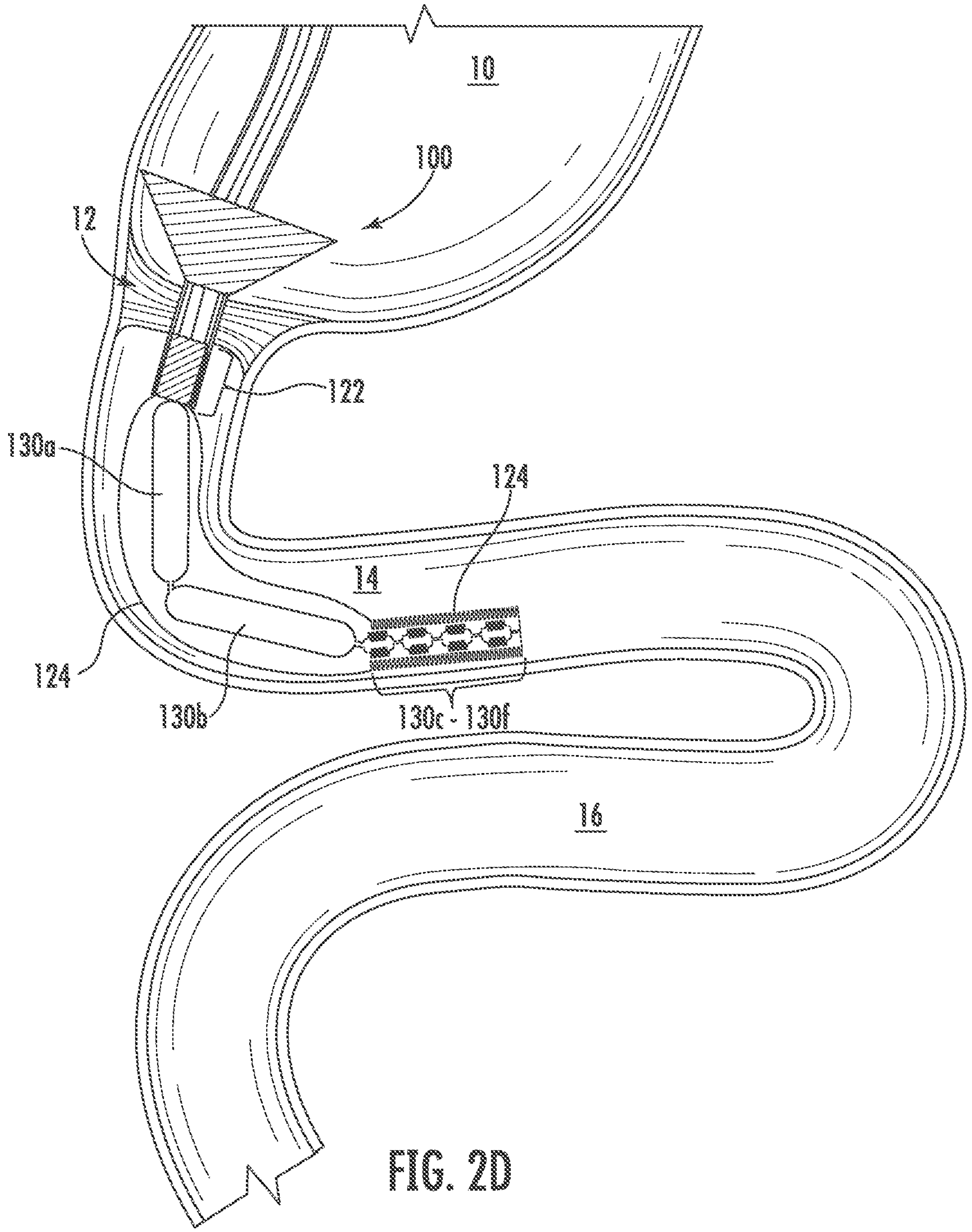
Figure 2E:
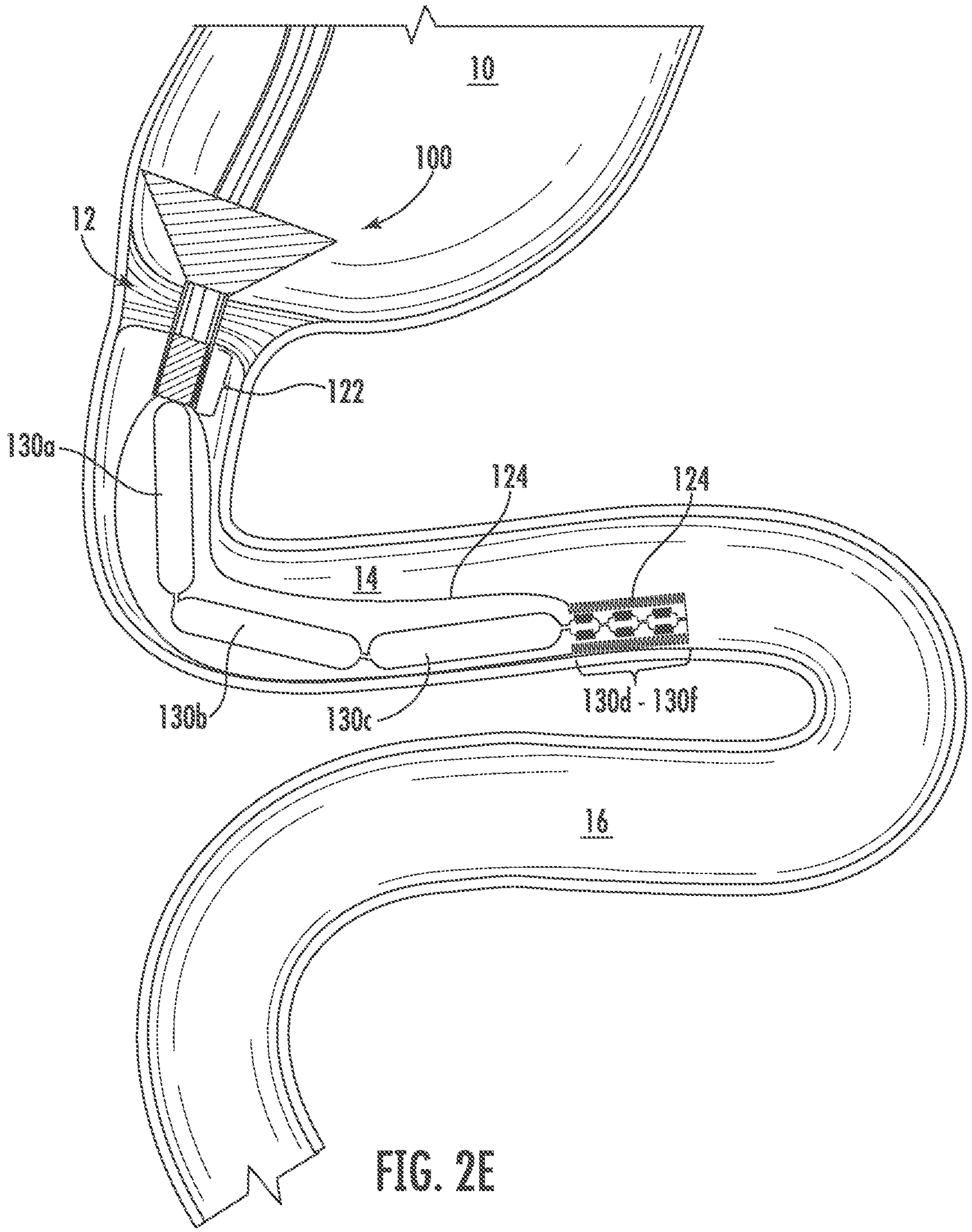
Figure 2F:
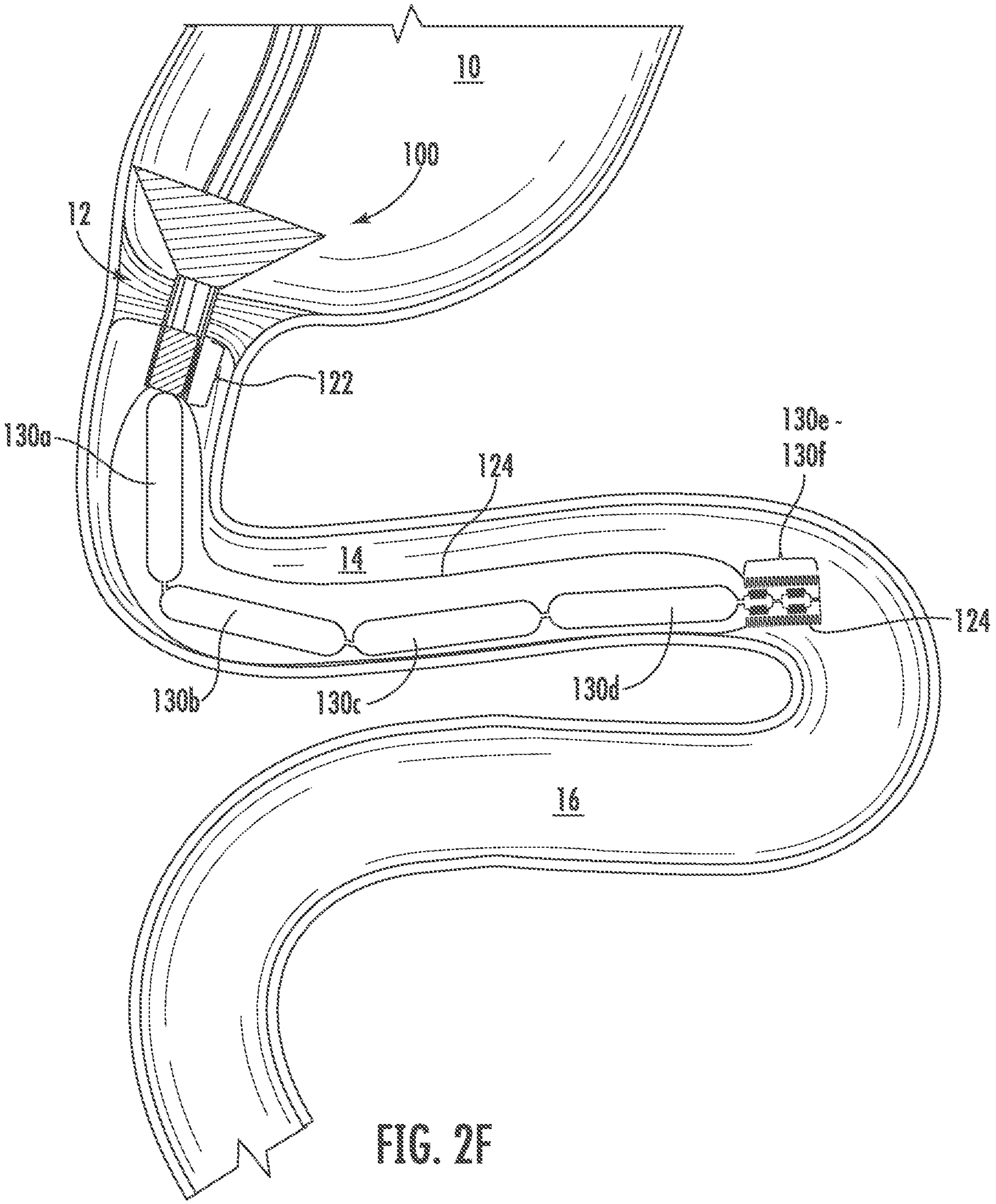

Referring to FIG. 2C, with the supported structure 122 of the medical device anchored across the pylorus 12, inflation fluid may be introduced from the fluid source 142 (FIG. 1A) through the fluid delivery lumen 140 (FIG. 1A) and into the proximal balloon 130*a* to move the proximal balloon 130*a* from the concertinaed configuration to a linearly expanded configuration. The concertinaed portion of the unsupported structure 124 disposed over and/or in contact with the proximal balloon 130*a* may also move from the concertinaed configuration to a linearly extended configuration as the linearly expanded proximal balloon 130*a* pulls the unsupported structure 124 distally through the duodenum 14 and towards the jejunum 16.

Figure 2G:
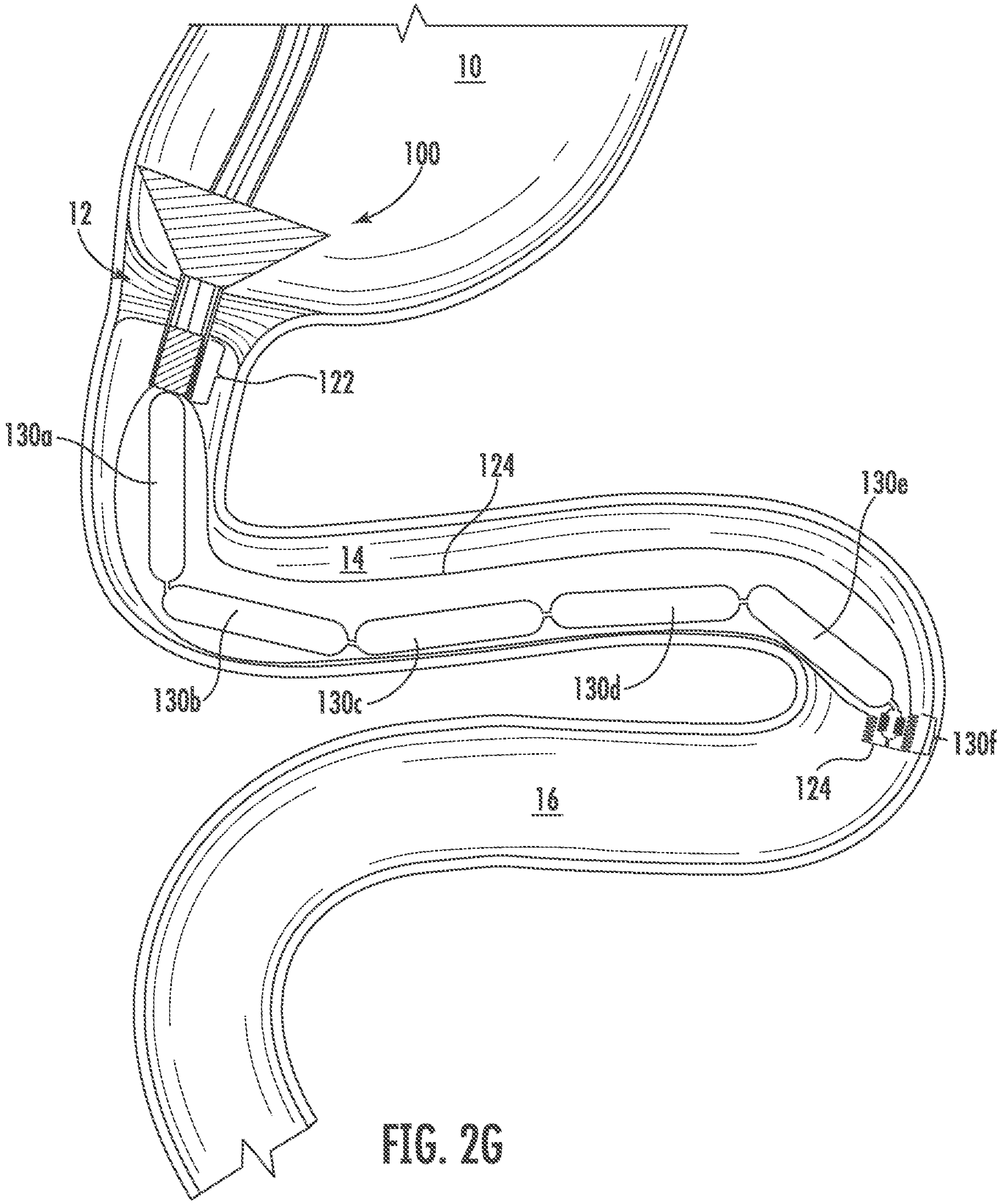
Figure 2H:
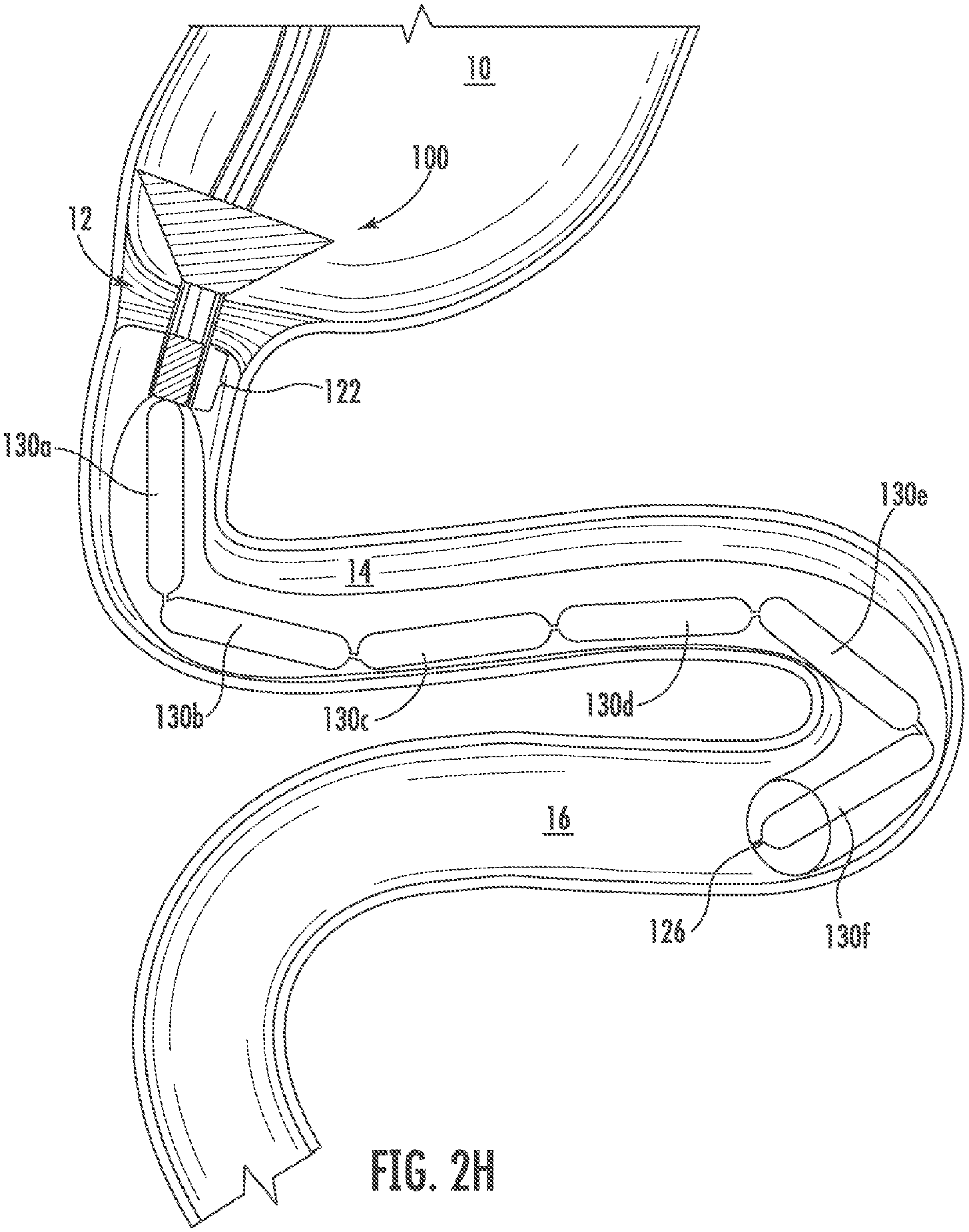

Referring to FIGS. 2D-2H, inflation fluid may continue to be introduced through the fluid delivery lumen 140 to sequentially inflate balloons 130*b* (FIG. 2D), 130*c* (FIG. 2E), 130*d* (FIG. 2F) and 130*e* (FIG. 2H) and 130*f* (FIG. 2H), and sequentially/incrementally move the corresponding concertinaed portions of the unsupported structure 124 disposed over and/or in contact each of the respective balloons 130*b*-130*f* 124 to a linearly extended configuration to track (e.g., pull, carry, etc.) the unsupported structure 124 further into the duodenum 14 towards the jejunum 16. Referring to FIGS. 2G-2H as exemplary embodiments, the flexible connector 136*d* connecting balloons 130*d* and 130*e* and the flexible connector 136*e* connecting balloons 130*e* and 130*f* may allow those balloons and the respective portion of the unsupported structure 124 to atraumatically bend or curve through a curved or tortuous portion of the duodenum 14.

Figure 2I:
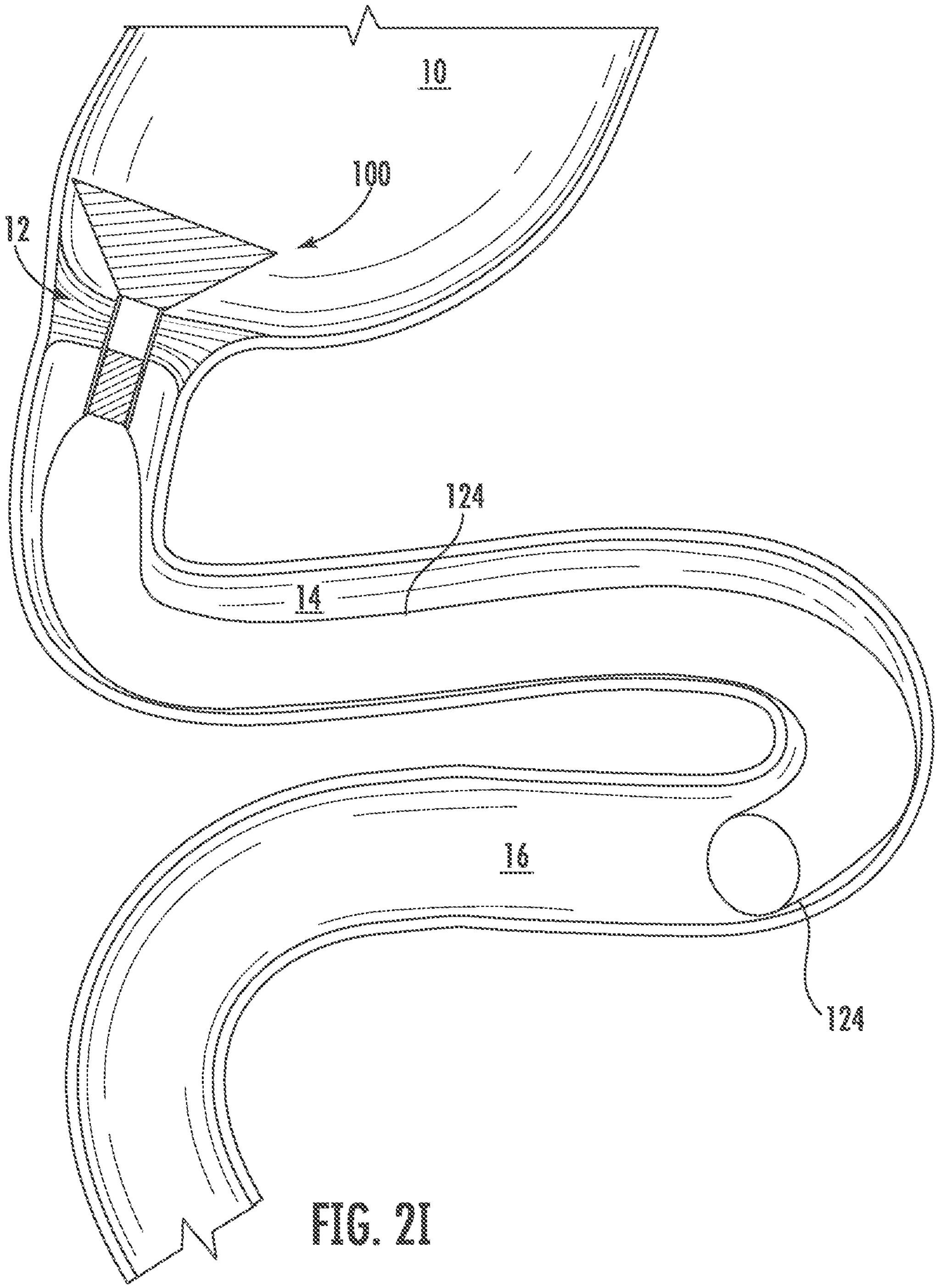

Referring to FIG. 2H, with the distal balloon 130*f* in the linearly expanded configuration, an attachment point between the distal end of the distal balloon 130*f* and the distal end of the unsupported structure 124 may be separated by activating a release mechanism 126, such as described above. Referring to FIG. 2I, the balloons 130*a*-130*f* may then be removed from within the patient, either in the linearly expanded configuration or in a deflated configuration, and the balloons 130*a*-130*f* and elongate member 110 removed from the patient. Alternatively, the balloons 130*a*-130*f* may remain in place within the unsupported structure, either in linearly expanded configuration or in a deflated configuration.

Figure 3A:
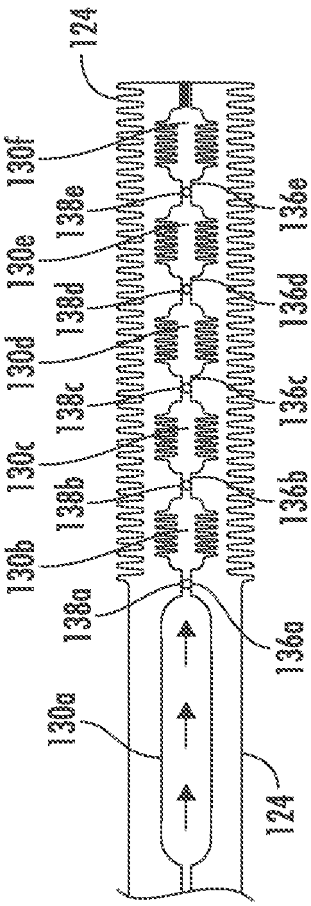
FIGS. 3A-3F provide perspective views of a medical device delivery system, according to one embodiment of the present disclosure.
Figure 3B:
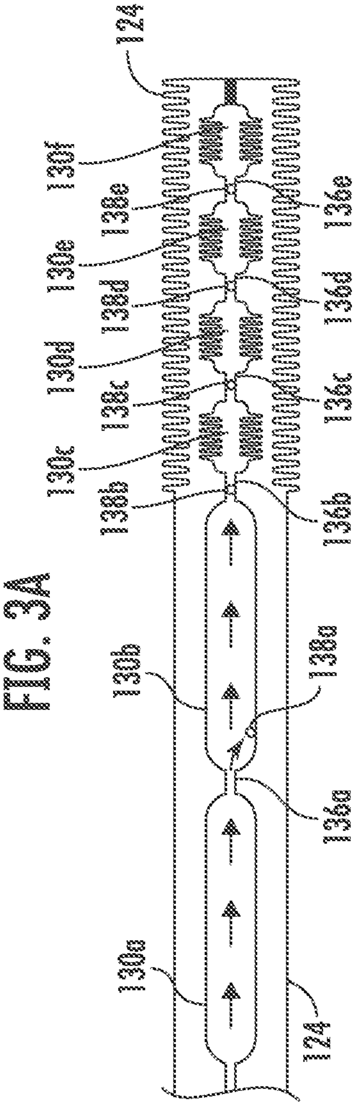
Figure 3C:
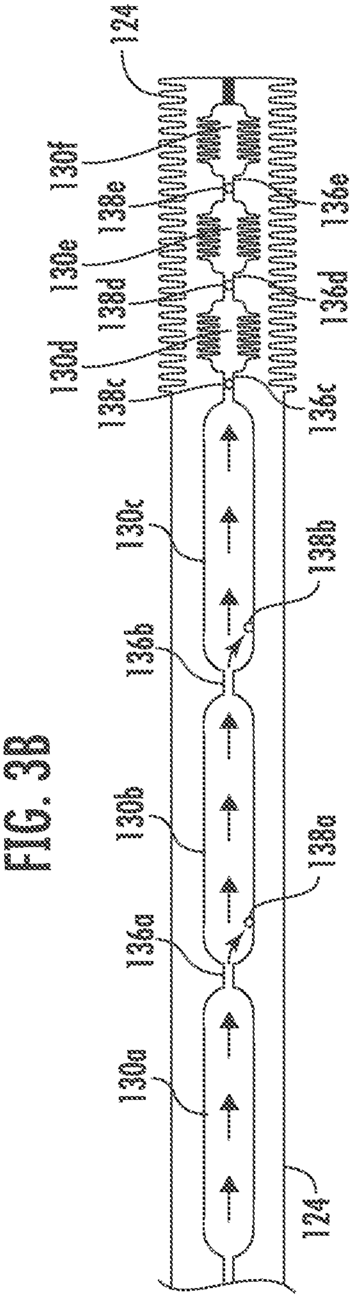
Figure 3D:
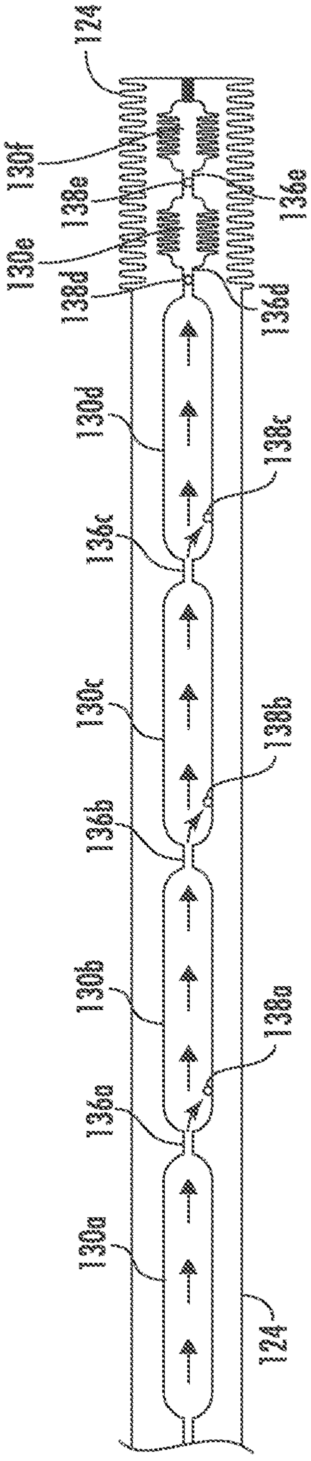
Figure 3E:
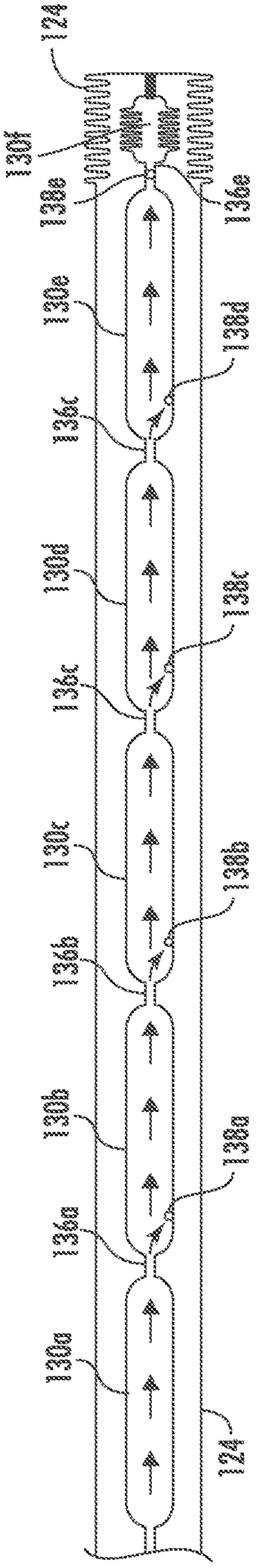
Figure 3F:
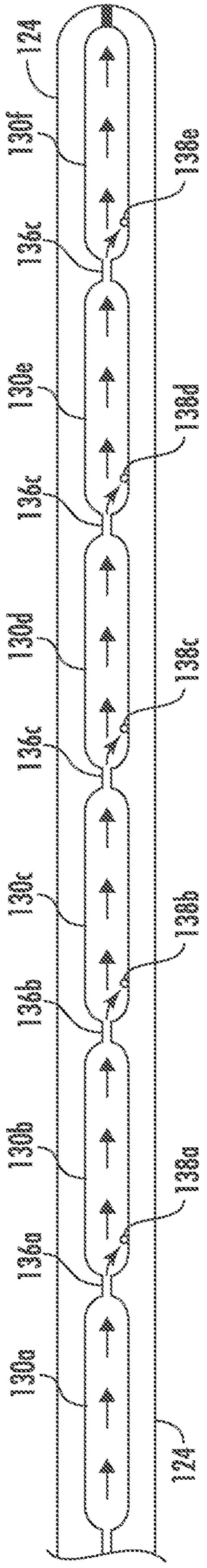

Referring to FIGS. 3A-3F, in one embodiment, a plug 138*a*, 138*b*, 138*c*, 138*d*, 138*e* (e.g., stoppers, corks, stopping balls, etc.) may be disposed within the lumens of the respective flexible connectors 136*a*, 136*b*, 136*c*, 136*d*, 136*e*. The plugs 138*a*-138*e* may be configured to prevent or limit the flow of inflation fluid into respective balloons 130*b*-130*f* until the immediately adjacent proximal balloon is fully inflated (e.g., linearly expanded), thereby further ensuring that the balloons sequentially expand in a proximal to distal direction to carry/pull the unsupported structure distally within the duodenum 14 towards the jejunum 16. For example, with the proximal balloons 130*a* in the linearly expanded (e.g., fully inflated) configuration (FIG. 3A) the internal pressure within the proximal balloon 130*a* may reach a threshold level to eject the plug 138*a* from within the lumen of the flexible connector 136*a* to allow inflation fluid to flow into and linearly expand the immediately adjacent balloon 130*b* (FIG. 3B). Inflation fluid may continue to be introduced to through the linearly expanded balloons to sequentially linearly expand the immediately adjacent balloons 130*c* (FIG. 3C), 130*d* (FIG. 3D), 130*e* (FIG. 3E) and 130*f* (FIG. 3F). In various additional embodiments, the flexible connectors 136*a*-136*e* may be twisted to close their respective internal lumens to prevent or limit the flow of inflation fluid into respective balloons 130*b*-130*f* until the immediately adjacent balloon is fully inflated.

In various embodiments, each of the balloons 130*a*-130*f* may include a length of approximately 40.0 mm and a width of approximately 6.0 mm in the linearly expanded configuration. In addition, the flexible connectors may include a length of approximately 5.0 mm and a lumen with an inner diameter of approximately 2.0 mm. Although the medical device delivery system 100 of the present disclosure includes six balloons with substantially identical sizes/shapes, in various embodiments the number of balloons and/or their respective lengths and diameters when linearly expanded may vary, including repeating or non-repeating patterns of long and short balloons, e.g., depending on the specific medical device and body lumen. For example, the unsupported structure 124 of the medical device 120 of the present disclosure may include an impermeable membrane extending approximately 600 mm past the pylorus and into a distal portion of the jejunum to prevent or limit absorption of nutrients across the wall of the duodenum and jejunum.

Although the medical device delivery system 100 of the present disclosure includes an inflation lumen configured to deliver inflation fluid (e.g., gas, liquid, gel, etc.) into the proximal-most balloon for sequential inflation of the balloons in a proximal to distal direction, in various embodiments the inflation lumen may extend over/along an outer surface of the plurality of balloons to deliver inflation fluid into the distal-most balloon for sequential inflation of the balloons in a distal to proximal direction.

In various additional embodiments, a medical device delivery system of the present disclosure may be configured to deliver a guidewire (rather than an unsupported structure of a medical device) within a body lumen. For example, the medical device delivery system may further include a contiguous lumen extending through the full length of the elongate member and through each of the plurality of balloons. The balloons may then be sequentially linearly expanded as discussed above to provide a contiguous guidewire lumen through which a guidewire may then be introduced. The balloons may then be retracted over the guidewire and removed from the patient, and a subsequent medical device tracked along/over the guidewire. Alternatively, the guidewire may be disposed within the contiguous lumen as the balloons are linearly expanded.

In various additional embodiments, the balloons 130*a*-130*f* of the present disclosure may be formed from or otherwise include a variety of flexible and non-compliant materials (e.g., silicone, polyethylene terapthelate (PET), nylon, hard rubbers, etc.) such that the balloons do not over-expand within the body lumen. In addition, or alternatively, rather than including a plurality of balloons, a medical device delivery system of the present disclosure may include a single elongate balloon disposed in a concertinaed configuration within the unsupported structure. The single elongate balloon may incrementally move from the concertinaed configuration to a plurality of incrementally increasing partially expanded configurations to track the unsupported structure through a body lumen.

In various additional embodiments, the balloons and/or unsupported structure may be collapsed, compacted and/or folded in a non-concertinaed configuration when in an undeployed (e.g., non-expanded or non-extended) state. In various embodiments, one or more of the balloons may be formed from a variety of non-compliant materials such that each balloon may move to a single pre-determined expanded configuration. Alternatively, one or more of the balloons may be formed from a variety of compliant materials such that each balloon may move to a variety of different expanded configurations. Although the balloons of the present disclosure are depicted including an expanded configuration with a cross-sectional dimension less than a corresponding inner dimension of the unsupported structure, in various embodiments one or more of the balloons may include an expanded configuration substantially equal to an inner dimension of the unsupported structure. In various embodiments, the balloons and/or the unsupported structure may be formed from a sufficiently pliable or flexible material (s) to allow the balloons and unsupported structure to bend or flex when advanced through tortuous body passages.

In various additional embodiments, fewer than all of the plurality of balloons may be linearly expanded when delivering the unsupported structure into a body lumen. For example, one or more of the balloons may remain in the concertinaed configuration once the unsupported structure is determined to have reached a desired portion of the body lumen. In various embodiments, one or more of non-expanded balloons may be moved to the expanded configuration during a subsequent medical procedure.

In various additional embodiments, the present disclosure is not limited to anchoring a medical device across the pylorus and delivering the unsupported structure into the duodenum. By way of non-limiting example, a medical device of the present disclosure may be anchored across an esophagus and the unsupported structure delivered through the stomach and across the pylorus into the duodenum.

All of the devices and/or methods disclosed and claimed herein can be made and executed without undue experimentation in light of the present disclosure. While the devices and methods of this disclosure have been described in terms of preferred embodiments, it may be apparent to those of skill in the art that variations can be applied to the devices and/or methods and in the steps or in the sequence of steps of the method described herein without departing from the concept, spirit and scope of the disclosure. All such similar substitutes and modifications apparent to those skilled in the art are deemed to be within the spirit, scope and concept of the disclosure as defined by the appended claims.

What is claimed is:

1. A medical device delivery system extending along a longitudinal axis between a proximal end and a distal end, the system comprising:

an elongate member having a proximal portion and a distal portion;

a medical device disposed within the elongate member, the medical device comprising a proximal structure, and a distal structure extending distally from a distal end of the proximal structure and having a wall with a proximal terminal end and a distal terminal end, the medical device configured to move from a first position, in which the proximal structure is disposed within the distal portion of the elongate member in a first configuration proximal to the distal structure, to a second position in which the proximal structure extends beyond a distal end of the elongate member and is expanded into a second configuration proximal to the distal structure;

a plurality of balloons disposed within the distal structure, and between the proximal terminal end of the wall of the distal structure and the distal terminal end of the wall of the distal structure when the medical device is in the first position; and a fluid delivery lumen having a proximal end configured to fluidly connect to a fluid source and a distal end in fluid communication with the plurality of balloons;

wherein:

balloons of the plurality of balloons are in collapsed configurations when the medical device is in the first position; and the wall of the distal structure is expandable, when the medical device is in the second position, from a first collapsed configuration over the plurality of balloons, into a second, longitudinally expanded configuration by expansion of at least one of the balloons of the plurality of balloons within the distal structure.

2. The medical device delivery system of claim 1, wherein:

the balloons of the plurality of balloons include a proximal balloon, a distal balloon, and one or more intermediate balloons extending between the proximal balloon and the distal balloon; and at least one of the balloons of the plurality of balloons is configured to expand distally outside and away from the proximal structure when the proximal structure is in the second configuration.

3. The medical device delivery system of claim 1, wherein:

the balloons of the plurality of balloons include a proximal balloon, a distal balloon, and one or more intermediate balloons extending between the proximal balloon and the distal balloon; and a proximal end of the proximal balloon includes an opening configured to fluidly receive the distal end of the fluid delivery lumen.

4. The medical device delivery system of claim 1, wherein:

adjacent balloons of the balloons of the plurality of balloons are attached by a flexible connector; and the flexible connector between the adjacent balloons includes a lumen extending through the flexible connector such that the adjacent balloons are in fluid communication with each other along a length of the plurality of balloons.

5. The medical device delivery system of claim 4, further comprising a plug removably disposed within the lumen of the flexible connector, wherein the plug is configured to prevent or limit a flow of an inflation fluid into one or more of the balloons of the plurality of balloons until a proximally adjacent balloon of the balloons of the plurality of balloons is in a longitudinally expanded configuration.

6. The medical device delivery system of claim 1, wherein:

the balloons of the plurality of balloons are collapsed in a concertinaed configuration and are configured to longitudinally expand from the concertinaed configuration sequentially from a proximal direction to a distal direction into a longitudinally expanded configuration; and the wall of the distal structure is configured to move from the first collapsed configuration distally into the second, longitudinally expanded configuration as the balloons of the plurality of balloons move from the concertinaed configuration to the longitudinally expanded configuration of the balloons of the plurality of balloons.

7. The medical device delivery system of claim 1, wherein the distal structure is formed of a layer of material including an impermeable membrane lacking rigidity and coupled to the proximal structure.

8. The medical device delivery system of claim 1, wherein the proximal structure includes one or more radially self-expanding portions and is configured to anchor the medical device across a pylorus of a patient within a body lumen when the medical device is in the second position, and the distal structure is coupled to the proximal structure to extend distally from the distal structure.

* * * * *